United States Patent [19]

Yu

[11] 4,409,239

[45] Oct. 11, 1983

[54] PROPYLENE GLYCOL DIESTER SOLUTIONS OF PGE-TYPE COMPOUNDS

[75] Inventor: Cheng-Der Yu, Mountain View, Calif.

[73] Assignee: Syntex (U.S.A.) Inc., Palo Alto, Calif.

[21] Appl. No.: 341,403

[22] Filed: Jan. 21, 1982

[51] Int. Cl.³ .................. A61K 31/215; A61K 31/19
[52] U.S. Cl. .................................... 424/305; 424/317
[58] Field of Search ................................ 424/305, 317

[56] References Cited

PUBLICATIONS

Hatachi et al.—Chem. Abst., vol. 83, (1975), p. 178,426v.

*Primary Examiner*—Sam Rosen
*Attorney, Agent, or Firm*—James M. Kanagy; Tom M. Moran

[57] ABSTRACT

Stable compositions of PGE and PGE-type compounds are achieved by dissolving these compounds in propylene glycol diesters of short chain fatty acids.

33 Claims, No Drawings

PROPYLENE GLYCOL DIESTER SOLUTIONS OF PGE-TYPE COMPOUNDS

BACKGROUND OF THE INVENTION

1. Field of the Invention

This invention relates to novel compositions of E-type prostaglandins in propylene glycol diesters of short chain fatty acids; and to a method for stabilizing E-type prostaglandin compounds in solution.

2. Related Disclosures

Prostaglandins have classically been described as chemically related 20 carbon chain hydroxy fatty acids having the basic skeleton of prostanoic acid:

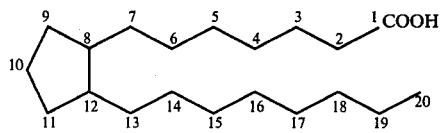

this structure is the basis for prostaglandin numbering and nomenclature.

Naturally occurring prostaglandins are derivatives of prostanoic acid. For descriptive purposes, four types are recognized. The type distinction is based primarily on pentane ring substituents and structural orientation. Although they can be named as derivatives of prostanoic acid, they are conventionally referred to by the letters A, B, E and F. Prostaglandins having an hydroxyl group at the C-11 position and a keto group at the C-9 position are known as PGE or PGE-type compounds. Those having hydroxyl groups at C-9 and C-11 are known as the PGF series and are further designated by an $\alpha$ or $\beta$ suffix to indicate the configuration of the hydroxyl group at said position. Series A and B have a keto group at C-9 and a double bond between C-10 and C-11 or C-8 and C-12 respectively. The natural compounds are the $\alpha$-hydroxy substituted compounds. Prostaglandins may contain different series of unsaturation in the molecule, particularly at C-5, C-13 and C-17. The unsaturation is also indicated by a suffix. Thus, for example, $PGF_1$ and $PGE_1$ series refer to prostanoic acids having a trans-olefin bond at the C-13 position, while the $PGF_2$ and $PGE_2$ series refer to prostadienoic acids having a cis-olefin bond at the C-5 position and a trans-olefin bond at the C-13 position. For a review on prostaglandins and the definition of primary prostaglandins, see for example, S. Bergstrom, Recent Progress in Hormone Research 22, pp. 153–175 (1966) and Science 157, p. 382 (1967) by the same author.

Prostaglandins generally act to stimulate gastrointestinal and reproductive smooth muscles, affect relaxation and contraction of respiratory smooth muscle, are hypotensives, and inhibit lipolysis of fatty acids, gastric acid secretion and blood platelet aggregation. There is not a precise structure-activity relationship in the prostaglandin family as much cross-activity is evident.

A great number of studies have been undertaken to enhance, extend and otherwise modify the activity of naturally occurring prostanoic acids. The majority of these studies have focused on modification of two areas, the two side chains and substituents attached to the cyclopropane moiety [see, for example, U. Axen et al., Synthesis Vol. 1, John Whilely and Sons Inc., New York, NY 1973 and P. H. Bently, Chem. Soc. Reviews, 2, 29 (1973)].

Of special interest to this invention is that group of prostaglandins which are labile in most standard pharmaceutical compositions, particularly PGE compounds and PGE-type compounds. In many instances the cyclopentane ring substituents substantially affect the prostaglandin's level of activity. Compounds which lose an oxygen from either C-9 or C-11 on the cyclopentane ring or which have these positions altered show altered levels of activity. For instance $PGE_2\alpha$, which has a carbonyl group at C-9 and an hydroxyl group at C-11 stimulates smooth muscle tissue but loss of the C-11 hydroxyl group to give a double bond in the cyclopentane ring, the PGA and PGB forms, show little or no such activity. This conversion is chemically facile because of the presence of the carbonyl group at C-9 in the PGE and PGE-type compounds which makes the hydroxyl group at C-11 labile to either base or acid dehydroxylation. The product of this dehydroxylation is a double bond conjugated with the carbonyl group of C-9, a stable chemical entity. Under acid conditions PGE-type compounds convert readily to the PGA form. Basic conditions cause PGE-type compounds to dehydroxylate and rearrange to the PGB form. In the case of $PGE_2$ type compounds this latter form is particularly stable because the C-9 carbonyl is now conjugated with the C-8/C-12 and C-13/C-14 double bonds. Similar degradation patterns have been observed in most compounds which have PGE-type cyclopentane ring substituents.

Initial efforts at providing easily dispensible dose formulations of prostaglandins, particularly for PGE-type compounds, met with difficulty. Aqueous PGE solutions were found to undergo rapid loss of activity when stored at temperatures above 0° C. at any pH, but particularly under alkaline conditions. Hydrous solutions adjusted to pH 5–7 were found to be most stable but loss of activity was still so rapid, drug concentrations after several months were very uncertain. Even in neutral or neat solutions there was found gradual degradation. Similar rapid degradation under these conditions have been observed in most compounds which have PGE-type cyclopentane ring substituents.

Various attempts have been made to formulate stable solutions of PGE-type compounds. Stabilization of these compounds has been observed in some solutions and in solid form at −20° C. or lower. More practical and usable alternative methods for stabilizing these prostaglandins have been developed and are described, for example, in U.S. Pat. Nos. 3,749,800; 3,826,823; 3,829,579; 3,851,052; 3,833,725 and 4,221,793. These patents teach the use of such solvents as lower molecular weight alcohols, polyalkylene glycols, dialkylated polyalkylene glycols, triacetin, dimethylacetamide and triethylcitrate respectively. See also Japanese patent application No. JA-123784 which discloses triglycerides for preparing stable prostaglandin compositions wherein the fatty acids are of intermediate chain length.

It has now been found that PGE and PGE-type prostaglandins can be prepared as stable pharmaceutical solutions by dissolving them in propylene glycol diesters of short chain fatty acids. Prostaglandins stabilized by such solvents are particularly adaptable for oral administration by soft-shelled gelatin capsules of therapeutic doses of prostaglandins.

SUMMARY

In a first aspect, this invention relates to a novel stable pharmaceutical composition of a PGE or PGE-type compound comprising a solution of said compound in a propylene glycol diester of short chain fatty acids.

A further aspect of this invention is a method for preparing a stable PGE or PGE-type pharmaceutical composition which method comprises dissolving a PGE or PGE-type compound in a propylene glycol diester of short chain fatty acids.

DESCRIPTION OF THE INVENTION

The solvents of this invention are propylene glycol diesters derived from short chain fatty acids which are saturated and unbranched aliphatic acids of 6 to 12 carbon atoms. Acids of particular interest are those derived from coconut oil which are of 6, 8, 10 or 12 carbon atoms in length. These acids are known as hexanoic, octanoic, decanoic and dodecanoic acid respectively. Commonly they are called caproic, caprylic, capric or lauric acid respecitvely. The word propylene glycol as used herein refers to the 1,2-dihydroxy propane compound which can alternately be called 1,2-propanediol.

Propylene glycol diesters of particular interest are those wherein the diester is a dicaprylate or a dicaprate, though the materials of this type which are generally available usually contain small amounts, e.g., up to about 0.5%, of the caproate and laurate. That is, an analysis of the dicaprylate may reveal the presence of a small amount of caproic acid and trace amounts of the other two acids while the dicaprate may additionally contait a small amount of lauric acid in addition to caprylic acid and trace amounts of caproic acid.

While it is possible to prepare and use a propylene glycol diester wherein the diester is either a dicaprylate or a dicaprate, the working of this invention does not require that the singular dicaprylate or dicaprate be employed in order tor achieve the stabilizing benefits of combining a PGE compound with these particlar solvents. However, such solvents are most readily available as mixtures of the two diesters, with small amounts of caproate and laurate. Because resolution of these mixtures into the component diesters would not materially add to the stabilizing qualities of these solvents, it is preferable to use such mixtures for the practice of this invention. This preference is not intended to effect the choice of diester or limit the amount of one diester which may be mixed with another for the practice of this invention.

Preparation of the subject propylene glycol diesters may be carried out by reacting the recited fatty acids with propylene glycol by methods common to the art for preparing esters. In addition, several commercial products are known and generally available.

Propylene glycol diesters may be prepared as the singular diester, i.e. propylene glycol dicaprate, by esterifying propylene glycol with capric acid under conditions commonly known in the synthetic chemistry art. Caproic, caprylic, capric and lauric acids are obtained by methods known in the art and are commercially available from various manufacturers. For example, caproic acid may be obtained according to the method set out in U.S. Pat. No. 3,173,933. Reference is made to U.S. Pat. Nos. 2,821,534 and 3,053,869 for methods relating to the production of caprylic acid. Methods for preparing capric acid are given, for example, in U.S. Pat. No. 2,964,933. Lauric acid can be obtained from various vegetable sources are noted in the Merck Index, 9th Ed. and is prepared by methods such as, for example, the one set out in U.S. Pat. No. 2,782,214. Propylene glycol is prepared by, for example, methods noted in the Merck Index, 9th Ed. but is commercially available from a number of chemical producers.

Propylene glycol diesters of this invention are generally recognized as safe (GRAS) by the U.S. Food and Drug Administration and have been approved as food additives by this agency. See 21 CFR 172.856. They are essentially tasteless and odorless.

It is preferred to use a commercial source of propylene glycol diester, particularly the dicaprylate/dicaprate solvent, in the practice of this invention. One commercial source of the preferred dicaprylate/dicaprate propylene glycol diesters is PVO International, Inc., Chemical Specialties Division, 416 Division St., Boongon, N.J. 07005 which markets such a product under the name Neobee M-20. This product has a typical aliphatic acid profile of 0.2% caproic acid, 68% caprylic acid, 31% capric acid, and 0.1% lauric acid. In addition, a similair propylene glycol diester solvent may be obtained commercially from Capital City Products Company, a division of Stokley Van Camp, Inc., P.O. Box 569, Columbus, Ohio 43216 under the name Captex 200. A typical aliphatic acid profile for this solvent will show about 74.4% caprylic acid, 24.2% capric acid and 0.13% lauric acid.

A general production process for the Neobee and Captex solvents is to hydrolyze coconut oil (a triglyceride ester), separate the free glycerine and fractionally distill the resultant fatty acids to obtain the caprylic and capric acids as a mixture. After adjusting the blend to the desired fatty acid ratios, the fractionated fatty acids are then re-esterified with 1,2-dihydroxy propane by commonly known chemical procedures to give the desired propylene glycol dicaprylate/dicaprate solvent.

The solvents of this invention may be used to stabilize all types of prostaglandin compounds but have the greatest utility for PGE and PGE-type compounds.

The phrase "PGE compounds" refers to those naturally occurring compounds which are derivatives of prostanoic acid and which have a C-9 carbonyl substituent and C-11 and C-15 hydroxyl substituents. These compounds have varying degrees of unsaturation as discussed above and all are intended to be included within the scope of the phrase "PGE compounds". There is intended to be included in this definition $PGE_1$, $PGE_2$, $PGE_3$ and dihydro-$PGE_1$ compounds. Esters of these compounds have been synthetically prepared, see for example U.S. Pat. Nos. 3,069,332 and 3,598,858.

There also have been prepared many compounds which retain the C-9 carbonyl and C-11 hydroxyl cyclopentane ring structural features but wherein the side chains have been modified; and which cause at least part of the biological response caused by PGE compounds. These compounds are intended to be included within the scope of this invention and are covered herein by the phrase "PGE-type compounds." Modified compounds differ from PGE compounds in one or more structural aspects, for example, in having one or more substituents, for example, alkyl, fluoro, phenyl, or cycloalkyl, on one or both side chains; in having fewer or more methylene groups in one or both side chains; in having a hetero atom, for example, oxygen in place of a side-chain methylene group; is having cis rather than a trans or a trans rather than a cis configuration for a side-chain carbon-carbon double bond; in having allenic double bonds in one side chain; or in any combination of those structural aspects. As examples of art which discloses such PGE-type compounds and others; see U.S.

Pat. Nos. 3,639,463; 3,759,978; 3,767,695; 3,781,325; 3,804,889; 3,812,179; 3,813,433; 3,833,640; 3,835,180; 3,842,118; 3,847,966; 3,849,487; 3,855,270; 3,864,387; and 4,178,457. See also German Offenlegungschrift Nos. 1,937,675; 1,937,921; 2,011,969; 2,036,471; 2,118,686; 2,121,980; 2,144,048; 2,150,361; 2,154,309; 2,165,184; 2,209,990; 2,217,044; 2,221,443; 2,317,019; 2,320,552; 2,322,673; 2,332,400; 2,345,685; 2,423,155 and 2,423,156. See also French Pat. No. 2,119,855, Belgian Pat. Nos. 779,898 and 782,822.

Also, for the purposes of this invention, it is intended to include racemic mixtures as well as resolved enantiomers of both PGE and PGE-type compounds.

In both instances it should be understood that not only the carboxlyic acids are to be included but also esters of said compounds. Those esters wherein the esterifying radical is alkyl of one to 12 carbon atoms, inclusive, cycloalkyl of 3 to 10 carbon atoms, aralkyl of 7 to 12 carbon atoms, phenyl, and phenyl substituted with 1, 2 or 3 chloro or alkyl of 1 to 4 carbon atoms are typical. Alkyl esters of 1 to 4 carbon atoms are particularly useful, especially methyl and ethyl esters.

Pharmaceutically acceptable salts of both compound groups are also to be included. These salts may be prepared from pharmaceutically acceptable non-toxic bases, including inorganic and organic bases. Salts derived from inorganic bases include, preferably, ammonium, potassium, sodium, calcium and magnesium salts. Preferred organic bases are isopropylamine, diethylamine, ethanolamine, piperidine, tromethamine, choline and caffeine.

Of particular interest are stable compositions of PGE-type compounds wherein the prostaglandins are 16-phenoxy and 16-substituted phenoxy prostaglandin E analogs represented by the following formula:

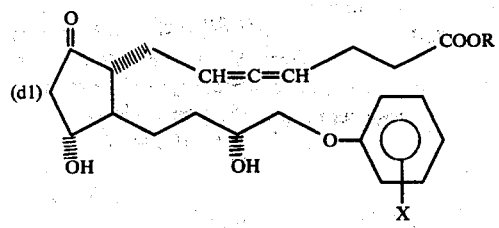

wherein R is hydrogen, a lower alkyl group of 1 to 4 carbon atoms, or the pharmaceutically acceptable, non-toxic salts of compounds in which R is hydrogen; and X is hydrogen, o-, m- or p-halo (fluoro, chloro or bromo), o, m- or p-methyl or o-, m- or p-methoxy.

The lines shown in the above formula and in the formulas below as " ≡ " indicate that the substituents are in α configuration, i.e., below the plane of the cyclopentane ring.

The double bond at C-13 has the same configuration as in natural prostaglandins of the PGE and PGF series, that is the trans configuration.

These novel compounds possess asymmetric centers and thus can be produced as racemic "(dl)" mixtures or as individual 8R-antimers. The racemic mixtures can be resolved if desired at appropriate stages by methods known to those skilled in the art, to obtain the respective individual antimers.

These particular compounds exhibit prostaglandin-like biological activity and thus are useful in the treatment of mammals where the use of prostaglandins is indicated. These compounds are useful for the control of asthmatic attack because they are bronchodilators and they also exhibit antiallergic properties by inhibition of mediator release. In addition, they are also useful for treating mammals for bronchial spasm or wherever bronchodilator compounds also exhibit vasodilator properties and are useful in controlling palpitating hypertension in mammals. They further exhibit central nervous system depressant activity in mammals, and are useful as sedatives. Most particularly, compounds of this formula have been found to be potent inhibitors of gastric secretion and ulcer induction and thus are extremely useful in the treatment and prevention of gastric and duodenal ulcers. The compounds are the subject of U.S. Pat. No. 4,178,457 which is incorporated herein by reference.

In the practice of this invention, prostaglandin concentrations may range from 0.001 to 100 mg/ml of chosen solvent. While the particular concentration for a given prostaglandin will depend on its inherent level of activity and the therepeutic dose to be administered at a particular time and by a particular route, a preferred concentration range will be between 0.01 mg/ml and 20 mg/ml. The most preferred concentration range is about 0.01 mg/ml to 5.0 mg/ml, particularly for the compounds represented by Formula II.

If a dosage form suitable for oral administration is desired, the prostaglandin/solvent composition may be encapsulated by art recognized methods in a pharmaceutically acceptable water dispersable material suitable for oral administration, for example, gelatin. Herein, soft gelatin capsules are the preferred oral dose form.

SPECIFIC EMBODIMENTS OF THE INVENTION

In the general case, the compositions of this invention are prepared by adding the prostaglandin to the propylene glycol diester solvent at the desired concentration and stirring the mixture at room temperature until a homogeneous solution is obtained. Such procedure provides an effective method for stabilizing PGE and PGE-type compound compositions. This procedure also acts as the first step in the process for dispensing, for oral administration, a PGE or PGE-type compound, the subsequent steps being to encapsulate the solution in a pharmaceutically acceptable water dispersable material suitable for oral administration and administering said vehicle in such a manner so as to administer a therapeutic dose to the subject.

The following examples set out general descriptions of means for practicing the invention as described herein.

EXAMPLE 1

To 10 ml of propylene glycol dicaprylate/dicaprate at 25° C. is added from about 0.01 to 10 mg of (dl)-9-keto-11α,15α-dihydroxy-16-phenoxy-17,18,19,20-tetranorprosta-4,5,13-trans-trienoic acid methyl ester. The mixture is stirred with a blade type stirrer until an homogeneous solution is obtained.

EXAMPLE 2

The products of Examples 1 may be utilized in an oral dosage form by adding the homogenous propylene glycol dicaprylate/dicaprate/trienoic acid methyl ester mixture to a soft-shelled gelatin capsule prepared by art recognized methods. The above mentioned compounds, in a variety of concentrations, are then typically administered for the reduction of gastric secretion and the prevention or healing of peptic ulcers in humans, or for other prostaglandin therapeutic uses.

EXAMPLE 3

A solution of 0.25 mg (dl)-9-keto-11α,15α-dihydroxy-16-phenoxy-17,18,19,20-tetranorprosta-4,5,13-trans-trienoic acid methyl ester per ml in propylene glycol dicaprylate/dicaprate (Captex 200) was made by dissolving said compound in the solvent with the aid of a magnetic stirrer. Aliquots of this solution were filled into glass ampules and sealed. The ampules were then stored at various temperatures for various durations. The following Table I shows percentage remainings of the initial drug concentration in these ampules after various durations of storage.

TABLE I
STABILITY OF AN E-TYPE*
PROSTAGLANDIN IN PROPYLENE
GLYCOL DICAPRYLATE/DICAPRATE (CAPTEX 200)

| Storage Time (month) | % Remaining of Initial Drug Concentration | |
| --- | --- | --- |
| | at 45° C. | at 60° C. |
| 0 | 100 | 100 |
| 1 | — | 97.6 |
| 3 | 100.7 | 90.0 |

These results indicate that (dl)-9-keto-11α,15α-dihydroxy-16-phenoxy-17,18,19,20-tetranorprosta-4,5,13-trans-trienoic acid methyl ester* is quite stable in Captex 200. As shown in the table, the drug solution retained 97.6% and 90.0% of its original drug concentration after 1 and 3 months storage at 60° C., respectively. In comparison, a 50 mcg solution of (dl)-9-keto-11α,15α-dihydroxy-16-phenoxy-17,18,19,20-tetranorprosta-4,5,13-trans-trienoic acid methyl ester per ml peanut oil, USP, gave 77.8% drug remaining after 2 weeks storage at 60° C.

What is claimed is:

1. A stable pharmaceutical composition of a PGE or PGE-type compound comprising a solution of said compound in a solvent comprising at least propylene glycol diester of short chain fatty acid.

2. A composition according to claim 1 wherein said compound is present in an amount between 0.001 mg to 100 mg/ml of solvent.

3. A composition according to claim 2 wherein said solvent comprises a propylene glycol dicaprylate or dicaprate or a mixture thereof.

4. A composition according to claim 2 wherein said solution is contained in a capsule of a pharmaceutically acceptable water-dispersible material.

5. A composition according to claim 4 wherein said water-dispersible material is gelatin.

6. A composition according to claim 2 wherein said compound is present in an amount between 0.01 mg to 20 mg/ml of solvent.

7. A composition according to claim 6 wherein said solution is contained in a pharmaceutically acceptable water-dispersible material.

8. A composition according to claim 7 wherein said solvent comprises a propylene dicaprylate or dicaprate or a mixture thereof.

9. A composition according to claim 6 wherein said water-dispersible material is gelatin.

10. A composition according to claim 2 wherein said compound is selected from those represented by the formula:

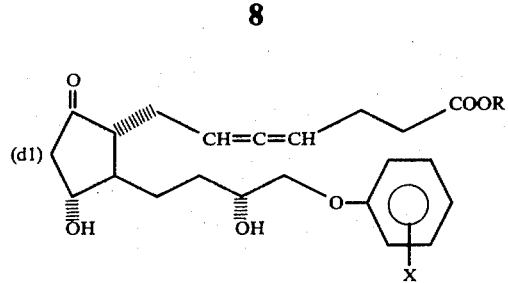

wherein:
R is hydrogen, a lower alkyl group of 1 to 4 carbon atoms, or the pharmaceutically acceptable, nontoxic salts of compounds in which R is hydrogen; and
X is hydrogen, o-, m- or p-halo, o, m- or p-methyl or o-, m- or p-methoxy.

11. A composition according to claim 10 wherein said compound is present in an amount between 0.01 mg to 20 mg/ml.

12. A composition according to claim 11 wherein said composition is encapsulated in gelatin.

13. A composition according to claim 12 wherein the compound is (dl)-9-keto-11α,15α-dihydroxy-16-phenoxy-17,18,19,20-tetranorprosta-4,5,13-transtrienoic acid methyl ester and is present in an amount between 0.01 mg to 5 mg/ml.

14. A method for preparing a stable soft-shell gelatin composition of PGE or PGE-type compounds which comprises dissolving at least one of said compounds in a solvent comprising at least one propylene glycol diester of a short chain fatty acid and adding the mixture to a soft-shelled gelatin capsule.

15. The method of claim 14 wherein said compound is present in an amount between 0.001 mg to 100 mg/ml of solvent.

16. The method of claim 15 wherein said solvent comprises a propylene glycol dicaprylate or dicaprate.

17. The method of claim 15 wherein said compound is selected from those represented by the formula:

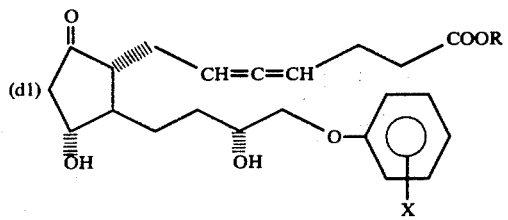

wherein:
R is hydrogen, a lower alkyl group of 1 to 4 carbon atoms, or the pharmaceutically acceptable, nontoxic salts of compounds in which R is hydrogen; and
X is hydrogen, o-, m- or p-halo, o, m- or p-methyl or o-, m- or p-methoxy.

18. The method of claim 17 wherein said compound is present in an amount between 0.01 mg to 20 mg/ml.

19. The method of claim 18 wherein said solvent comprises a propylene glycol dicarylate or dicaprate or mixtures thereof.

20. The method of claim 19 wherein said compound is (dl)-9-keto-11α,15α-dihydroxy-16-phenoxy-17,18,19,20-tetranorprosta-4,5,13-trans-trienoic acid methyl ester and is present in an amount between 0.01 mg to 5 mg/ml.

21. A method for preparing a stable PGE or PGe-type pharmaceutical composition which method comprises dissolving a PGE or PGE-type compound in a propylene glycol dicaprylate or dicaprate solvent or mixtures thereof.

22. The method according to claim 21 wherein said compound is present in an amount between 0.001 mg to 100 mg/ml of solvent.

23. The method according to claim 22 wherein said solvent comprises a propylene glycol dicaprylate or dicaprate or mixtures thereof.

24. The method according to claim 22 wherein said solution is contained in a capsule of a pharmaceutically acceptable water-dispersible material.

25. The method according to claim 24 wherein said water-dispersible material is gelatin.

26. The method according to claim 25 wherein said compound is present in an amount between 0.01 mg to 20 mg/ml of solvent.

27. The method according to claim 26 wherein said solution is contained in a pharmaceutically acceptable water-dispersible material.

28. The method according to claim 27 wherein said water-dispersible material is gelatin.

29. The method according to claim 22 wherein said compound is selected from those represented by the formula:

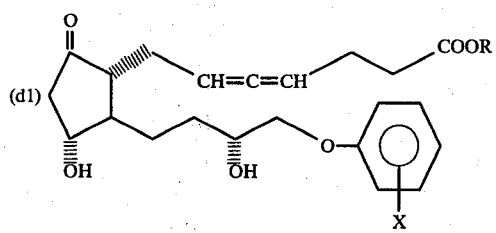

wherein:
R is hydrogen, a lower alkyl group of 1 to 4 carbon atoms, or the pharmaceutically acceptable, non-toxic salts of compounds in which R is hydrogen; and
X is hydrogen, o-, m- or p-halo, o, m- or p-methyl or o-, m- or p-methoxy.

30. The method according to claim 29 said compound is present in an amount between 0.01 mg to 20 mg/ml.

31. The method according to claim 30 wherein said composition is encapsulated in gelatin.

32. The method according to claim 31 wherein said solvent comprises propylene glycol dicaprylate or dicaprate or mixtures thereof.

33. The method according to claim 32 wherein said compound is (dl)-9-keto-11α,15α-dihydroxy-16-phenoxy-17,18,19,20-tetranorprosta-4,5,13-trans-trienoic acid methyl ester and is present in an amount between 0.01 mg to 5 mg/ml.

* * * * *